[19] United States Patent
Katsumata et al.

[11] Patent Number: 5,601,806
[45] Date of Patent: Feb. 11, 1997

[54] METHODS FOR SCAVENGING ACTIVE OXYGEN COMPOUNDS AND PREVENTING DAMAGE FROM ULTRA VIOLET B RAYS USING TAURINE ANALOGUES

[75] Inventors: Manabu Katsumata; Keiko Kiuchi, both of Kanagawa-ken; Tomoyasu Tashiro, Tokyo; Saburo Uchikuga, Kanagawa-ken, all of Japan

[73] Assignee: Sogo Pharmaceutical Company Limited, Tokyo, Japan

[21] Appl. No.: 309,139

[22] Filed: Sep. 20, 1994

Related U.S. Application Data

[62] Division of Ser. No. 994,960, Dec. 22, 1992, abandoned.

[30] Foreign Application Priority Data

Dec. 27, 1991 [JP] Japan .................................. 3-357993
Sep. 22, 1992 [JP] Japan .................................. 4-276789

[51] Int. Cl.$^6$ .......................... A61K 7/42; A01N 37/12; A01N 33/02; C01B 17/64
[52] U.S. Cl. .......................... 424/59; 514/665; 514/562; 514/917; 514/860; 514/886; 562/29; 560/150; 252/188.28
[58] Field of Search .......................... 252/188.28; 562/29; 560/150; 424/59; 514/665, 562, 917, 860, 886

[56] References Cited

U.S. PATENT DOCUMENTS

| | | | |
|---|---|---|---|
| 4,508,733 | 4/1985 | Moreuil | 514/578 |
| 4,563,479 | 1/1986 | Feuer et al. | 514/562 |
| 4,847,069 | 7/1989 | Bissett et al. | 424/47 |
| 5,000,945 | 3/1991 | Kobayashi et al. | 524/59 |

FOREIGN PATENT DOCUMENTS

| | | |
|---|---|---|
| 108854 | 11/1982 | European Pat. Off. . |
| 140943 | 4/1987 | European Pat. Off. . |

OTHER PUBLICATIONS

Masayasu Inoue et al, "Antioxidants in Therapy and Preventive Medicine", Edited by I. Emerit et al, Plenum Press, New York, Mar. 1990.

Inoue, M. et al, "Vascular Function and Injuries", edited by T. Sato, Fujita Kikaku Press, 1991, pp. 356–371.

C.R. Acad. Sc. Paris, t. 302, "Oceanographie biologique", Serie III, No. 13, 1986, pp. 503–508.

Black, H. S. (1987), "Potential involvement of free radical reactions in ultraviolet light–mediated cutaneous damage", Photochemistry and Photobiology, vol. 46, No. 2, pp. 213–221.

Ogura, R. et al (1987), "Role of oxygen in lipid peroxide of skin exposed to ultraviolet light", in The Biological Role of Reactive Oxygen Species in Skin, ed. by Hayaishi et al, Univers. of Tokyo Press, pp. 55–63.

Garner, M. H. et al (1980), "Selective oxidation of cysteine and methionine in normal and senile cataractous lenses", Proc. Natl. Acad. Sci. USA, vol. 77, No. 3, pp. 1274–1277.

Fischer, L. J. et al (1980), "Inhibition of Alloxan action in isolated pancreatic islets by superoxide dismutase, catalase, and a metal chelator", Diabetes, vol. 29, pp. 213–216.

(List continued on next page.)

Primary Examiner—Sharon Gibson
Assistant Examiner—Joseph D. Anthony
Attorney, Agent, or Firm—Browdy and Neimark

[57] ABSTRACT

Taurine analogues are used for scavenging active oxygen compounds and preventing and minimizing damage to the skin from ultraviolet rays. The taurine analogues have the following formula:

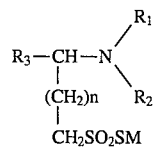

wherein $R_1$, $R_2$ and $R_3$ are as defined in the specification.

3 Claims, 4 Drawing Sheets

OTHER PUBLICATIONS

Asayama, K. et al (1984), "Alloxan–induced free radical production in isolated cells", Diabetes, vol. 33, pp. 1008–1011.

Masayasu Inoue and Nobukazu Watanabe, Targeting SOD by Gene and Protein Engineering and Inhibition of Oxidative Stress in Various Diseases, "Antioxidants in Therapy and Preventive Medicine", I. Emerit, ed., pp. 5–12, Plenum Press New York (1990).

Mousa, H. M. et al, "Alternative Sulfur Donors for Detoxification of Cyanide in the Chicken", Comparative Biochemistry and Physiology, vol. 99, pp. 309–315 (1991).

Costa, M. et al, "Displacement of [3H]GABA binding to bovine brain receptors by sulfur–containing analogues", Neurochemistry International, vol. 17, pp. 547–551 (1990).

METHODS FOR SCAVENGING ACTIVE OXYGEN COMPOUNDS AND PREVENTING DAMAGE FROM ULTRA VIOLET B RAYS USING TAURINE ANALOGUES

This is a division of parent application Ser. No. 07/994,960, filed Dec. 22, 1992 now abandoned.

DETAILED DESCRIPTION OF THE INVENTION

1. Field of the Invention

The present invention relates to active oxygen scavengers, and more particularly, it relates to active oxygen scavengers unknown to the prior art, whose active ingredients are taurine analogues, especially aminothiosulfonic acids. The present invention provides not only a prophylactic and/or therapeutic agent for each of the diseases concerned with active oxygens but also an excellent dermatologic preparation, which contain an aminothiosulfonic acid compound.

2. Description of the Prior Art

In recent years, environmental pollution, particularly air pollution due to, for example, from gas, has caused holes in the ozone layer, leading to an increase in harmful ultraviolet rays reaching the earth's surface. Much attention has been given recently to the harm produced by ultraviolet rays, which includes, in addition to the harm which has been known in the past, the production of active oxygen (superoxides, hydrogen peroxide, hydroxy radicals, singlet oxygen, hypochlorous acid), and free radicals (lipidperoxide radicals, lipid alkoxy radicals, lipid radicals), resulting from photopoisoning and oxygen toxicity when the skin is exposed to ultraviolet rays. This is because these are one cause of photoaging and photocarcinogenesis.

Also, active oxygens produced in cells and not due to photopoisoning are thought to be causative substances of other various diseases. Active oxygens have functions which cause, for example, circulatory diseases such as myocardial infarct, arrhythmia, arteriosclerosis, etc.; respiratory diseases such as pneumonia, smoking disorders, etc.; diseases of the cranial nervous system such as cerebral edema, cerebral infarct, cerebral hemorrhage, etc.; digestive diseases such as acute gastric mucosal disorders, gastric ulcers, cirrhosis, pancreatitis, etc.; blood system diseases such as leukemia, hemoglobinopathy, septicemia, etc.; endocrine system diseases such as diabetes, stress reactions, etc.; urological diseases such as glomerular nephritis, hemolytic renal disorders, etc.; supportive tissue diseases such as articular rheumatism, autoimmune diseases, etc.; ophthalmological diseases such as cataract, corneal ulcer, etc.; and diseases due to radiation damage.

It has ardently been desired to develop, using the technology presently available in the art, an effective system capable of handling diseases related to active oxygens, including oxygen toxicity and photoaging; yet at present such development has not been satisfactorily achieved. The present invention utilizes specific aminothiosulfonic acids to protect against diseases related to active oxygens, such as oxygen toxicity and photoaging, in a completely novel system unknown to the prior art.

SUBJECT MATTER OF THE INVENTION

It is an object of the present invention to develop a novel system for the prevention of diseases relating to active oxygen, such as photopoisoning and oxygen toxicity, by scavenging active oxygens and free radicals which are produced by harmful ultraviolet rays.

Figure 1:
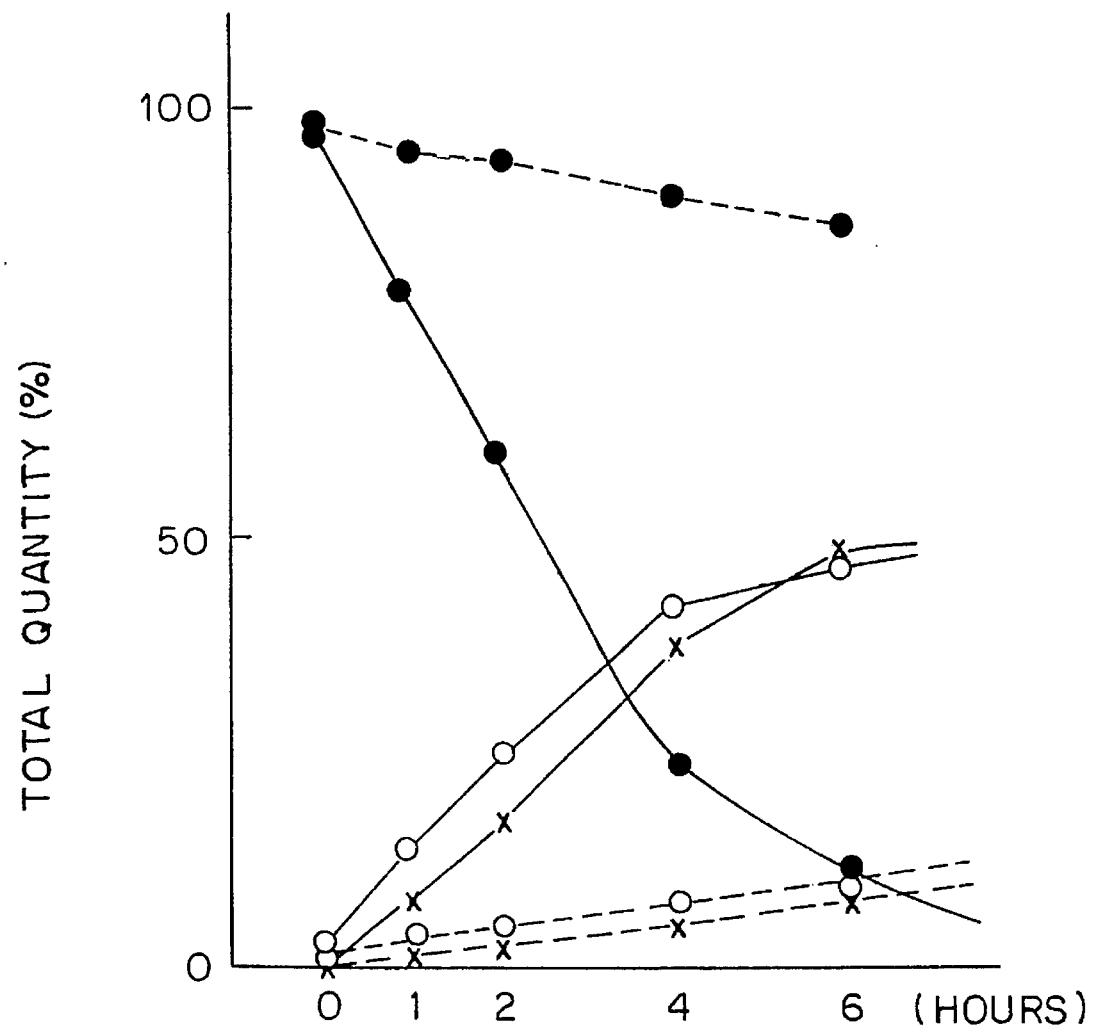
FIG. 1

A graph illustrating the effect of the addition of thiotaurine and NaN3 to the Rf/hv system.

FIG. 2

A graph illustrating the influence of thiotaurine on peroxidation of methyl linolenate.

FIG. 3

A graph illustrating the inhibitory effect of thiotaurine on methionine photooxidation (HO.).

FIG. 4

A chromatogram showing the oxidation of thiotaurine with $H_2O_2$.

MEANS TO SOLVE THE POINTS OF ISSUE

The multi-faceted research undertaken in order to achieve the above mentioned object resulted in a preference towards the use of natural substances, and upon a zealous screening of substances having anti-oxygen toxicity and anti-photoaging properties, we succeeded in discovering a taurine analogue present in a marine organism, as a substance possessing anti-oxygen toxicity and anti-photopoisoning properties.

In other words, we the inventors of the present invention have discovered that an aminothiosulfonic acid compounds, which are stable under normal conditions, react with active oxygens and free radicals which are produced by visible light rays or ultraviolet rays, into sulfur and aminosulfonic acids (for example, taurine). The colloidal, insoluble substance (sulfur), which is a byproduct of the reaction, displays both an ability to screen out light to eliminate direct light rays, as well as a bactericidal function.

The details regarding the reason or mechanism for this must await further research, but as Chemical formula 4 below indicates, it is supposed that the reaction of aminothiosulfonic acid→aminosulfinic acid+sulfur→aminosulfonic acid is promoted, resulting in the above mentioned light screening, bacteriocidal effects and production preventing or scavenging functions against active oxygens and free radicals.

Chemical Formula 4

Photodecomposition System for Aminothiosulfonic Acid

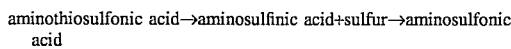

aminothiosulfonic acid→aminosulfinic acid+sulfur→aminosulfonic acid

Active oxygens and free radicals are associated with light radiation and cause damage to the skin, but it is possible to reduce the skin damage due to light radiation by applying a scavenger against active oxygens and free radicals. For example, by local application of a scavenger against active oxygens and free radicals, it is possible to prevent erythema and edema. Also, anti-oxidizing agents and scavengers are effective to halt the production of sun-burned cells, erythema and lipid peroxides (Photochemistry and Photobiology, vol. 46, No. 2, pp. 213–221, 1987; Potential involvement of free radical reactions in ultraviolet light-mediated cutaneous damage).

The present invention was finally completed as a result of verifying the excellent anti-oxygen toxicity, anti-photopoisoning and light screening functions of aminothiosulfonic acids, as the above and following observations make clear.

The active ingredient compound used in the present invention is an aminothiosulfonic acid compound represented by Chemical formula 5 below.

Chemical formula 5

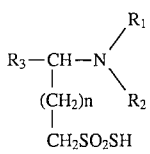

wherein $R_1$ and $R_2$ may be identical or different, each representing a hydrogen atom, a saturated or unsaturated linear or branched alkyl or acyl group with carbon number 1–22, or an amidino group;

$R_3$ represents a hydrogen atom or —$COOR_4$, where $R_4$ represents a hydrogen atom, a saturated or unsaturated linear or branched alkyl group with carbon number 1–22, or alkali metal or alkaline earth metal;

and n represents either 0 or 1.

In this active ingredient compound, $R_1$ and $R_2$ may be selected from the group consisting of alkyl groups with carbon number 1–22, including methyl, ethyl, propyl . . . eicosyl, heneicosyl and docosyl groups, as well as unsaturated alkyl groups derived therefrom, or branched saturated or unsaturated alkyl groups similarly derived therefrom; acyl groups derived from each of these various alkyl groups (formyl, acetyl, propionyl, butyryl, valeryl . . . stearoyl, oleoyl groups, etc.); amidino groups; and hydrogen. $R_3$ represents a hydrogen atom or $COOR_4$, and $R_4$ also represents one of the alkyl groups mentioned above with carbon number 1–22, a hydrogen atom or a metal. Also, the metal may be sodium, potassium, calcium, magnesium or any other alkali metal or alkaline earth metal.

The active ingredient compound according to the present invention may be produced by any appropriate method heretofore known, and examples include, but are not limited to, the following: thiotaurine, dimethylthiotaurine, diethylthiotaurine, monomethylthiotaurine, monoethylthiotaurine, thiotaurocyamine, laurylthiotaurine, alanine thiosulfonate, and salts thereof.

Active oxygens liberated in a living body must be rapidly consumed. Otherwise, various cell elements such as DNA, lipids and proteins become the target molecules for oxidation, and breakdown of the functions of the cells accompanies the production of lipid peroxides. The body possesses systems for the elimination of these active oxygens, of which superoxide dismutase (SOD), catalase, and glutathione peroxidase (GSH-Px) are known. Of these, SOD has attracted much attention as a catalyst of the reaction shown below, decomposing and detoxifying superoxides (Chemical formula 6, below), thus lowering the amount of lipid peroxides (LPO) in the epidermis due to UV rays, when applied externally to the skin (R. Ogura et. al., The Biological Role of Reactive Oxygen Species in Skin, edited by O. Hayaishi, S. Imamura and Y. Miyachi, University of Tokyo Press, 1987, p. 55).

Chemical formula 6

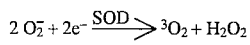

Further, recent observations have revealed that intravenously injected SOD derivatives prevent or considerably alleviate cerebral ischemic disorders, myocardial ischemic disorders, acute gastric mucosal disorders, carrageenin edema, hemorrhagic shock, cerebral edema, renal ischemic disorders, etc. (M. Inoue and N. Watanabe: "Antioxidants in Therapy and Preventive Medicine," edited by I. Emerit, Plenum Press, 1990, p. 5; M. Inoue, N. Watanabe and S. Kawamoto: "Vascular Functions and Injuries," edited by T. Sato, Fujita Kikaku Press, 1991, p. 356).

It would seem to be that the determination of whether a given compound has functions similar to SOD, or has a SOD activating function, is extremely important when considering its use for the elimination of active oxygen or the suppression of lipid peroxide production, or for the suppression in turn of erythema due to ultraviolet (UV) rays which is thought to be attributable thereto, and for preventive and therapeutic effects against diseases related to superoxides.

The results of our investigation into the SOD-like functions and SOD activating function of thiotaurine are described below.

Experiment 1: SOD-Mimic Functions of Thiotaurine

Experimental method: Measurement of the SOD-mimic functions was done, with slight modifications, according to the Xanthine-xanthine oxidase-nitrobluetetrazolium (NBT) method described in Lipid Peroxide Experiments (edited by N. Kaneda, N. Ueda, Ishiyaku Press, p. 144). The measurement is based on measuring at 560 nm the amount of formazan produced by the reduction of NBT with a superoxide which results from the oxidation of xanthine with xanthine oxidase, and calculating the activation thereof. The modification involved irradiation with UVB (6.0 mW/cm$^3$.5 min, 1.8 J/cm$^2$, 313 nm) for 5 minutes while simultaneously adding the xanthine oxidase, in order to interrupt the reaction. The results are shown in Table 1.

TABLE 1

| | SOD-like function of thiotaurine | | | | | |
|---|---|---|---|---|---|---|
| | Concentration (M/reaction solution) | | | | | |
| | $10^{-7}$ | $10^{-6}$ | $10^{-5}$ | $10^{-4}$ | $10^{-3}$ | $10^{-2}$ |
| thiotaurine | 34.7* | 47.0 | 35.7 | 43.2 | 34.7 | 34.4 |

Unit: Abssorbance(Abs.)
Superoxide production inhibition rate (%)

The above results showed a SOD-mimic function for thiotaurine, irrespective of its concentration. These results confirmed the effectiveness of thiotaurine in scavenging superoxides.

Next, a measurement was made of the SOD activating function. First, 4 test tubes were prepared, and the measurement was done according to the compositions and procedures listed in Table 2 below.

TABLE 2

Method of measurement of SOD activating function

|  | (1) | (2) | (3) | (4) |
|---|---|---|---|---|
| Na$_2$Co$_3$ Buffer | 2.2 | 2.2 | 2.2 | 2.2 |
| Xanthine | 0.1 | 0.1 | 0.1 | 0.1 |
| EDTA | 0.1 | 0.1 | 0.1 | 0.1 |
| BSA | 0.1 | 0.1 | 0.1 | 0.1 |
| NBT | 0.1 | 0.1 | 0.1 | 0.1 |
| Test Comp. | 0.1 | 0.1 | — | — |
| SDO | 0.1 | 0.1 | 0.1 | — |
| DIW | — | 0.1 | 0.1 | 0.2 |
| Preincubate 25° C., 10 min. | | | | |
| XOD | 0.1 | — | 0.1 | 0.1 |
| UVB radiation, 6.0 mw/cm$^2$, 5 min. (1.8 J/cm$^2$) | | | | |
| CuCl$_2$ | 0.1 | 0.1 | 0.1 | 0.1 |

Unit: (ml)
(1) System for observing whether the consumption of superoxides by SOD is further increased with the test composition.
(2) Blank for (1)
(3) System for inhibiting XOD reaction with SOD. XOD reaction was 20% inhibited by SOD.
(4) System for a complete, uninhibited XOD reaction.

The SOD activation rates of the test compositions were calculated using the equation listed as Equation 1 below, and the results shown in Table 3 were obtained.

$$SDO \text{ activation rates}(\%) = \left\{ \frac{4-(1-2)}{4-3} - 1 \right\} \times 100 \quad \text{Equation 1}$$

TABLE 3

SOD activating function of thiotaurine

| | Concentration (M/reaction solution) | | | | |
|---|---|---|---|---|---|
| | 10$^{-6}$ | 10$^{-5}$ | 10$^{-4}$ | 10$^{-3}$ | 10$^{-2}$ |
| thiotaurine | 1.6 | 14.3 | 29.6 | 32.1 | 65.8 |

Unit: (%)

As the above results make clear, thiotaurine activated SOD concentration-dependently. This verifies the fact that thiotaurine functions to activate SOD and scavenge active oxygen.

Next an investigation was made regarding thiotaurine's reactivity with (ability to eliminate) singlet oxygen ($^1O_2$), and regarding the peroxidation of methyl linoleate. The following experiments are examples showing clearly that thiotaurine scavenged $^1O_2$ by reacting therewith, and that the peroxidation of lipids is suppressed in a concentration-dependent manner. Experiment 2 is described below to prove the reaction of thiotaurine with $^1O_2$.

Experiment 2: Reactivity of Thiotaurine with $^1O_2$ (Riboflavin (Rf)/hv-System)

Fourteen milligrams of thiotaurine and 1.5 mg of riboflavin (Rf) were dissolved in 50 ml of a wing buffer solution (pH 7.8), after which light irradiation (FL20SBRF Toshiba, UVA 0.1 mW/cm$^2$, UVB 0.1 mW/cm$^2$, visible light 0.4 mW/cm$^2$) was initiated in the presence and in the absence of 34 mg of sodium azide (NaN$_3$). After continuously reacting the product from the reactant solution with dansyl chloride, a fluorescent reagent, high-performance liquid chromatography was used for separation and analysis.

The conditions for the high-performance liquid chromatography were as listed below.

Column: Inertsil ODS-2
Mobile phase: 0.1M phosphate buffer solution: THF (tetrahydroxyfuran): acetonitrile=670:40:350
Flow rate: 1.0 ml/min
Ex: 305–395 nm
Em: 480 nm The results obtained are shown in FIG. 1 as percentages (%) for the proportions of thiotaurine, hypotaurine and taurine at each hour shown.

It is assumed that in the Rf/hv-system $^1O_2$ is produced according to the formula listed below as Chemical formula 7.

Chemical Formula 7

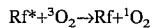

Rf*: Riboflavin in excited state
Rf: Riboflavin in ground state

First, thiotaurine (●—●) underwent decomposition when reacted with $^1O_2$ produced as described above, being 40% reacted in 2 hours, and 90% reacted in 6 hours in the absence of NaN$_3$, $^1O_2$ quencher while the amounts of hypotaurine (○—○) and taurine (x—x) increased. In contrast, in the presence of NaN3 and with $^1O_2$ production suppressed, thiotaurine (●—●) underwent almost no decomposition, with approximately 85% remaining at 6 hours.

This indicates that $^1O_2$ plays a part in the path of decomposition of thiotaurine - taurine.

An experiment using only a single type of system or quencher is not enough to solidly prove that $^1O_2$ contributes to a given reaction. Therefore, the 3 systems listed below were used in identical experiments.
1. Riboflavin/hv-system, 1,4-diazabicyclooctane (DABCO) as $^1O_2$ quencher
2. Rose bengal/hv-system DABCO as $^1O_2$ quencher
3. Methylene blue/hv-system DABCO as $^1O_2$ eliminator The results proved that thiotaurine reacts with $^1O_2$ in all three systems, itself converting to hypotaurine and taurine.

Lipid peroxides are known to play a key part in aging and carcinogenesis through destruction of organic membranes and the deactivation of oxygen. Below are shown experiments conducted to determine whether or not thiotaurine suppresses the production of lipid peroxides.

Experiment 3: Lipid Peroxide Production Inhibitory Effect of Thiotaurine

Figure 2:
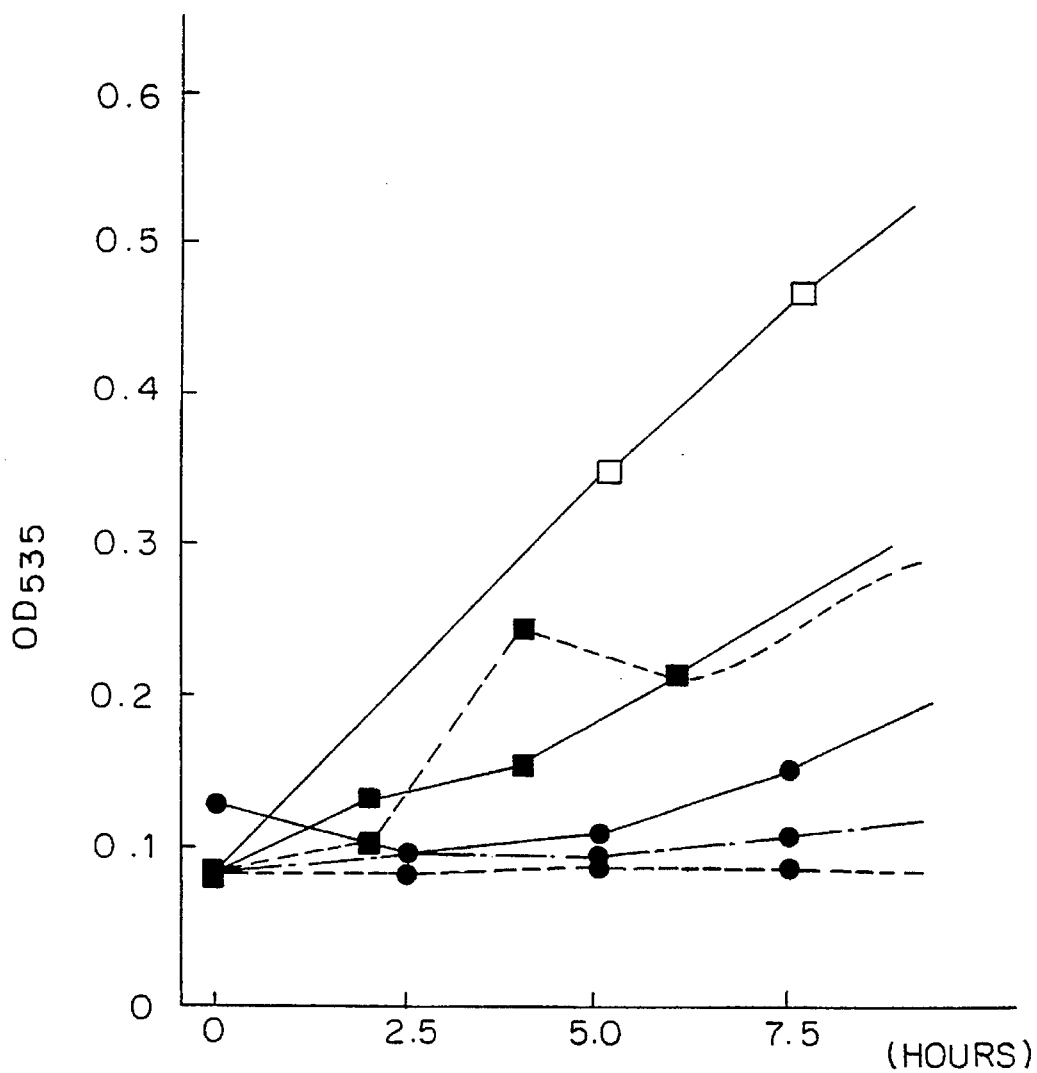

Fifty ml of a solution prepared by combining a solution of 12.5 mg of methyl linoleate, 2.5 mg of Rf and 2–70 mg of thiotaurine in ethanol with a wing buffer solution, and the resulting solution was subjected to light irradiation as in Experiment 2. After a determined period of time a sample was recovered, and the lipid peroxides were measured using the Yagi method. The results are shown in FIG. 2.

As these results make clear, thiotaurine present at a quantity of 2.8×1/10$^4$M prevented approximately 50% of the production of lipid peroxides after 7.5 hours, suppressing lipid peroxide production in a concentration-dependent manner. At a quantity of 4×1/10$^3$M the production was almost 100% prevented.

Thus, it was clearly indicated that thiotaurine also has a strong production suppressing effect against lipid peroxides, a causative substance of aging and cancer.

The retina is one of the tissues in the body containing high numbers of flavin compounds, but in recent years the methionine residue of a lens protein is reported to be oxidized to methionine sulfone or methionine sulfoxide in senile cataracts (Proc. Natl. Acad. Sci. U.S.A., 77 (3), 1274–1277, 1980).

Also, the photoreceptor-rich outer layer has a very high concentration of taurine, which is released into the aqueous humor upon light irradiation, suggesting that aminothiosulfonic acids according to the present invention exhibit an excellent anti-oxidizing function as a mechanism against the photo-oxidation of such types of proteins and amino acids. This is described below.

Figure 3:
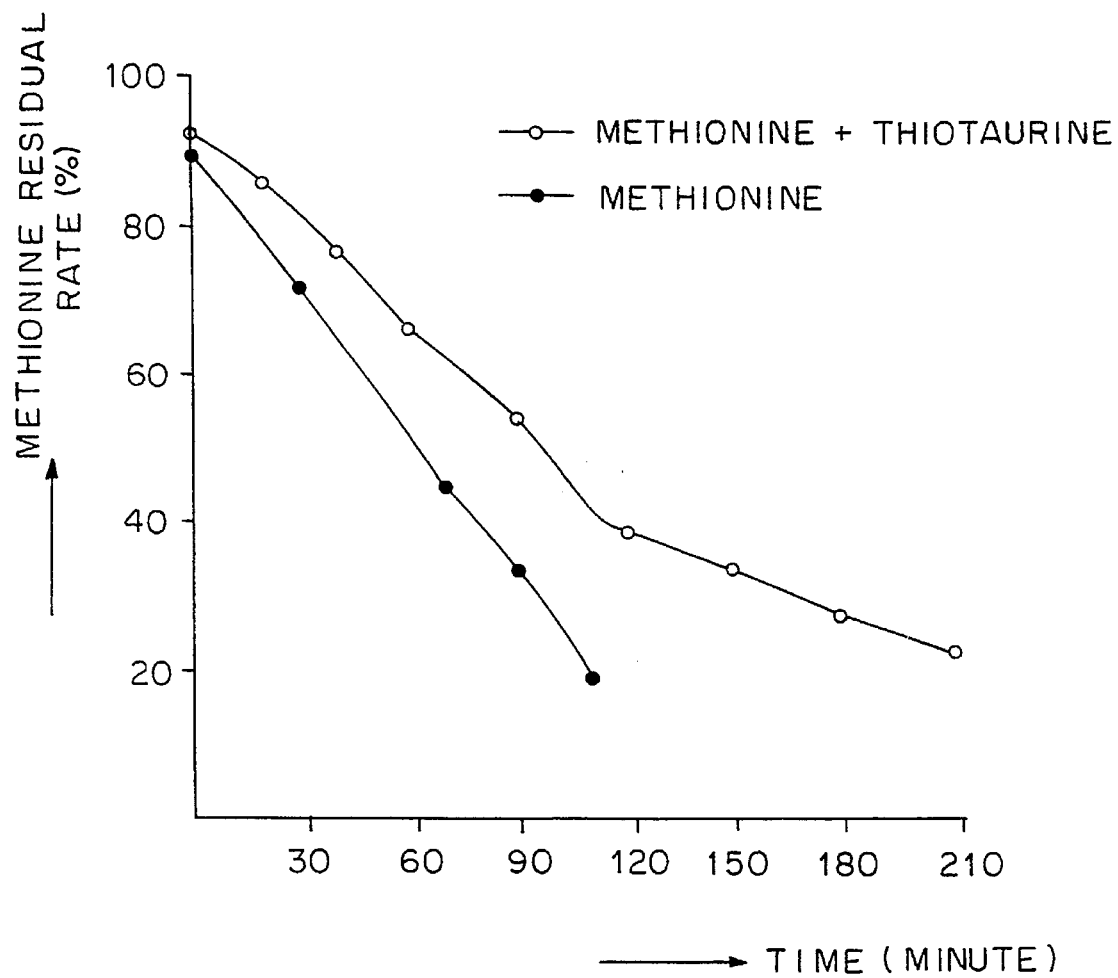

Experiment 4: Preventing Effect of Thiotaurine on the Photo-oxidation of Amino Acids In a quartz cell was placed 1 mM of methionine, riboflavin, NADH and Fe (II) EDTA, and super high pressure mercury lamp rays (UVA 370 nm) were irradiated thereto, thus presenting a control. Next, 1 mM of thiotaurine was added to the same system mentioned above and the reaction was initiated by light irradiation as before, while the two reactions were sequentially followed by HPLC and finally compared. The results are shown in FIG. 3.

These systems, to which the Fe (II) chelate compound and electron donor, NADH, were added in the presence of riboflavin, produced the HO. (hydroxyl radical) which is the most dangerous and highly active of the active oxygens. Here the scavenging effect was observed for thiotaurine. As a result, it was determined that thiotaurine inhibits the methionine oxidation with HO., and has a scavenging effect against hydroxy radicals.

$H_2O_2$ is an active oxygen, and in addition to its own known toxicity, it produces the most highly reactive HO. of active oxygens in an aqueous solution containing bivalent iron, as shown in Chemical formula 8 below, or as shown in Chemical formula 10 when it is present in an appropriate proportion as compared with the substance of Chemical formula 9 below and an iron ion or when a chelate such as EDTA is present.

Chemical Formula 8

$Fe^{2+}+H_2O_2 \rightarrow Fe^{3+}+HO.+OH^-$

Chemical Formula 9

$O_2^-$

Chemical Formula 10

$O_2^-+H_2O_2 \rightarrow HO.+OH^-+O_2$

A description will now be given regarding the $H_2O_2$ scavenging function of thiotaurine.

Experiment 5: $H_2O_2$ Scavenging Function of Thiotaurine

Figure 4:
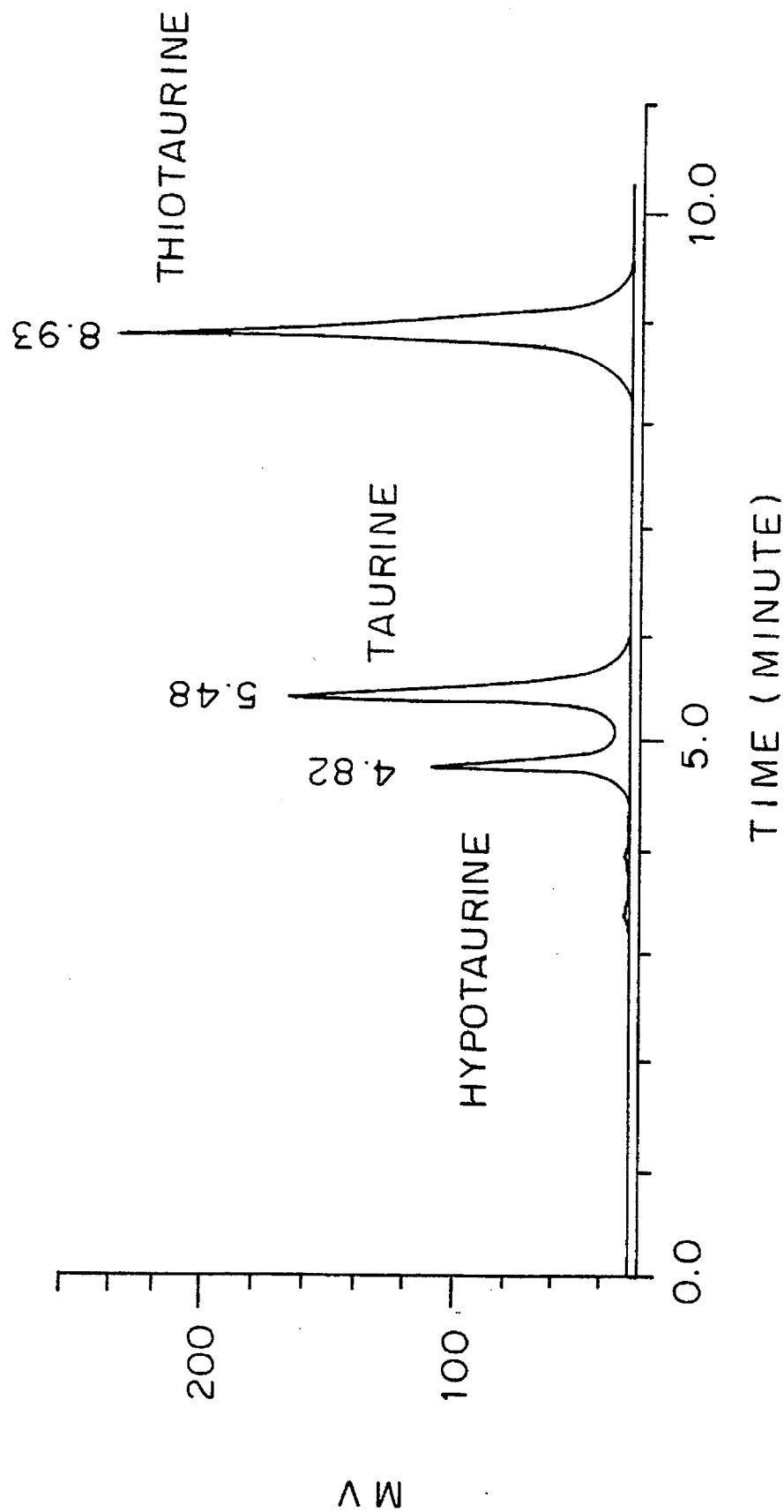

In a quartz cell were placed 1 mM of thiotaurine and 1 ELM of $H_2O_2$, and the change in thiotaurine was measured by HPLC while irradiating with light. The results obtained are shown in FIG. 4. As these results clearly show, thiotaurine was oxidized to taurine and hypotaurine after about 3 hours of light irradiation, and since the oxidation was effected with $H_2O_2$, it was determined that thiotaurine has an eliminating effect on $H_2O_2$. With no light irradiation, however, thiotaurine did not react at all.

Concerning the Inhibiting Effect of Thiotaurocyamine on the Oxidation of Tyrosine, in the Presence of Ultraviolet Light Rays The production of tyrosine oxide polymers, a cause of hyperpigmentation of the skin, are initiated by the oxidation of tyrosine to DOPA or dopa quinone, the latter being further oxidized to dopa chrome. These reactions are accelerated by $^1O_2$ or by a substance of Chemical formula 11 listed below. We the inventors of the present invention discovered that the active ingredient of the present invention exhibits an inhibiting effect on the above mentioned tyrosine oxidation. The results are described as follows.

Chemical formula 11

$O_2^-$

Experiment 6: Tyrosine Oxidation Preventing Effect

In a quartz cell was put 1 ml of L-tyrosine (30 mg/100 ml), 1 ml of a tris buffer solution and 0.9 ml of a test solution ($6.25 \times 1/10^2$ mol/l–1 mol/l), and the mixture was allowed to stand under radiation from an ultraviolet lamp at 37° C. for 10 minutes. Following this, 0.1 ml of tyrosinase (2000 units/ml) were added thereto, and further irradiated under an ultraviolet lamp at 37° C. for 30 minutes, after which the production of tyrosine oxide polymers was measured at 475 nm. The results are listed in Table 4.

TABLE 4

| Tyrosine oxidation inhibiting effect of thiotaurocyamine | | |
|---|---|---|
| Concentration | Inhibition rate (%) | |
| (mol/l) | Indoors | Ultraviolet rays |
| $6.25 \times 10^{-2}$ | 12.8 | 78.0 |
| $1.25 \times 10^{-1}$ | 36.8 | 88.2 |
| $2.5 \times 10^{-1}$ | 61.7 | 92.8 |
| $5 \times 10^{-1}$ | 87.7 | 92.4 |
| 1 | 91.5 | 96.6 |

As the above results clearly show, the production inhibiting effect of thiotaurocyamine on tyrosine oxide polymers when ultraviolet rays were used was considerably greater than that of the reaction using indoor lighting. It inhibited the production of active oxygen through photooxidation with ultraviolet radiation, which leads to the acceleration of tyrosine oxidation. This effect was strong even at low concentration.

By this we determined that thiotaurine suppresses the production of active oxygens and free radicals in vitro, but next animals were used to demonstrate the same in in vivo experiments.

Experiment 7: Influence of Externally Applied Thiotaurine on UVB Rays

Thiotaurine was added to a base cream of the composition indicated in Table 5, at concentrations of 5.0% (w/w) and 7.5% (w/w), respectively.

TABLE 5

| Composition of cream (g) | |
|---|---|
| MGS-B | 1.2 |
| BB-5 | 0.5 |
| BB-20 | 1.2 |

TABLE 5-continued

| Composition of cream (g) | |
|---|---|
| Bees Wax Gold | 3.0 |
| GM-18S | 2.0 |
| Butyl alcohol | 1.0 |
| CIO | 18.0 |
| 1,3-BG | 5.0 |
| Sodium dehydroacetate | 0.1 |
| Water | 68.0 |

Experimental method: In this experiment, male Hartley guinea pigs of body weight 230–250 g were used. The back, abdomen and side hair of the guinea pigs was first roughly removed with hair clippers, after which the hair was completely removed with care using a Brown electric shaver. On the morning of the next day, the hair was again removed, the body weights measured, and the groups divided. The UVB radiation was applied in 10 stages of 0.075, 0.1, 0.15, 0.2, 0.3, 0.4, 0.5, 0.6, 0.7, and 0.8. Five minutes prior to irradiation, the base cream was applied to the control area, and the thiotaurine-containing cream preparations were applied to the test area. Then observations were made 2, 4, 6, 8, and 24 hours later to determine the presence of erythema, visually.

Criteria: In conformity with Table 6 below, the results are displayed as Sun Protection Factors (Table 7 given below).

Table 6

Criteria

0; No erythema

1; Difficult to determine presence or absence of erythema

2; Erythema clearly present but edges unclear

3; Erythema clearly present and edges clear

4; Erythema with edema

TABLE 7

| | Change in SPF values | | | | |
|---|---|---|---|---|---|
| | Post-irradiation time (hr) | | | | |
| | 2 | 4 | 6 | 8 | 24 |
| 5% thiotaurine | 3.6 | 3.6 | 3.8 | 4.1 | 5.0 |
| 7.5% thiotaurine | 4.4 | 4.3 | 4.3 | 4.3 | 5.7 |

The above results clearly show that the use of the 5% thiotaurine cream for 2 hours produced an SPF value of 3.6, which gradually increased to a final SPF value of 5.0 at the end of 24 hours. Also, a similar and even stronger effect was observed when applying the 7.5% thiotaurine cream.

Even when applied externally as described above, thiotaurine clearly has a considerable erythema preventing function.

Next, the therapeutic effect of thiotaurine against chick embryo cataract induced by hydrocortisone is demonstrated by the following experiment.

Experiment 8: Effect of Thiotaurine on Hydrocortisone Induced Chick Embryo Cataract White leghorn chick embryos were incubated in an incubator at a temperature of 37° C. and a humidity of approximately 70%. Then a solution of 0.12 mg of hydrocortisone succinate (HC) in 0.2 ml of purified water was administered through the air chambers of the eggs of the control group and the test group on the 15th day of incubation. Thiotaurine was then given to the test group 2 hours, or 2 and 5 hours, after HC administration.

The lenses were removed 8 hours after HC administration, and the presence of cataracts was judged according to the criteria listed in Table 8, using the method of Nishikuni, et. al. (Investigative Opthamology and Visual Science, 25, p. 1051, 1984). The results obtained thereby are shown in Table 9 below.

Table 8

Criteria

I. Lens was clear and indistinguishable from control.

II: Lens had a faint opaque ring between the cortical region and the nuclear region.

III: Lens had a distinct opaque ring between both regions.

IV: Pinhole-sized clear area in an opaque nucleus.

V: An opaque nucleus.

TABLE 9

| Cataract preventing effect of thiotaurine | | | | | |
|---|---|---|---|---|---|
| | Determination | | | | |
| | I | II | III | V | IV |
| Normal group | 6/6 | | | | |
| Control group (HC 0.12 mg/egg) | | | | | 6/6 |
| Medicated groups | | | | | |
| Thiotaurine 0.5 mg × 1 time/egg | | 6/8 | 2/8 | | |
| Thiotaurine 1.0 mg × 1 time/egg | 2/8 | 2/8 | 4/8 | | |
| Thiotaurine 1.0 mg × 2 times/egg | 4/8 | 4/8 | | | |
| Thiotaurine 2.0 mg × 2 times/egg | 4/8 | 4/8 | | | |

When 0.12 mg of HC was given on the 15th day of incubation, grade V cataracts were observed in all the eyes by the 17th day. Verification was thus made of the improving effect of thiotaurine on cataracts.

In cataracts, active oxygen functions to convert a polyvalent unsaturated fatty acid (PUFA) into a PUFA radical (PUFA.), which then reacts with an oxygen molecule to become a fatty acid peroxide radical (PUFA00.). The hydrophilic lipid peroxides produced within the hydrophobic lipid double membrane causes a change in the permeability of the membrane, and the resulting disturbance of the homeostasis of the cell produces cataracts. It is thought that thiotaurine suppresses the outbreak of cataracts by scavenging the active oxygen.

Concerning pancreatic diseases, it has been reported that active oxygens contribute the onset of experimental I-type diabetic models, caused by alloxan or streptozotocin. Particularly with alloxan, it is believed that active oxygens play an important part in the origin of diabetic symptoms, based on the fact that superoxides are produced in vitro, that the symptoms of diabetes are suppressed through SOD or catalase administration (L. J. Fischen and S. A. Hamburger, Diabetes, 29, p. 213, 1980), and that the luminescence from the pancreatic islet on other tissues at the time of alloxan administration is of high strength when an investigation is made using the chemiluminescence method (K. Asayama, F. Nyfeler, D. English et al., Diabetes, 33, p. 1008, 1980).

The effect of thiotaurine on alloxan diabetes is demonstrated in the following experiment.

Experiment 9: Effect of Thiotaurine on Alloxan Diabetes

Thiotaurine was orally administered in an amount of 500 mg/kg once a day to Wistar Imamichi rats, for a period of 2 weeks. Three days prior to the last administration of the medicine feeding of the rats was stopped for 16 hours, and alloxan dissolved in chilled physiological saline was intravenously injected at an amount of 75 mg/kg. One hour after the last administration of the medicine, the rats were killed, their blood was obtained, and a measurement was made of the triglycerides and blood sugar in the blood, using the enzyme method. The results obtained are shown in Table 10.

TABLE 10

Effect of thiotaurine on alloxan diabetes

|  | Triglyceride (mg/dl) | Blood sugar (mg/dl) |
|---|---|---|
| Normal group | 109.9 ± 13.6 | 132.6 ± 4.2 |
| Control group | 521.9 ± 134.6 (100) | 1182.0 ± 196.7 (100) |
| Thiotaurine Administered group | 363.8 ± 38.2* (70) | 769.1 ± 120.3* (65) |

*$P < 0.05$ vs control group

The above results show that thiotaurine significantly suppressed the increase of triglycerides in diabetes to 70%, and that of glucose to 65% as compared with the values found in the control, confirming its ability to improve alloxan diabetes.

The results of the animal experiment listed as Experiment 7 indicate that thiotaurine has a strong erythema suppressing effect.

It is said that prostaglandins, active oxygens and free radicals are either directly or indirectly involved in the occurrence of erythema due to UVB. These in vivo results are supported by the functions of thiotaurine demonstrated in vitro; namely, SOD-mimic function, SOD-activating function, scavenging function against the substances of Chemical formula 12 below (Experiment 1), $^1O_2$ scavenging function (Experiment 2), lipid peroxidation inhibitory function (Experiment 3), and scavenging function against the substances of Chemical formula 13 below (Experiment 4).

Chemical formula 12

$$O_2^-$$

Chemical formula 13

.OH

The active ingredient compound according to the present invention, an aminothiosulfonic acid, not only functions as a light shield and as a production inhibitor or scavenger of lipid peroxides and active oxygen, but since it and its decomposition products are structurally similar to compounds which are naturally present in the body including taurine, etc. (C.R. Acad. Sci., Ser. 3, 302 (13) 503–8: Presence of Large Quantities of Thiotaurine and Hypotaurine in the Tissues of *Riftia pachyptila*), its toxicity is extremely low making it a safe substance. Actually, even when 200 mg/kg of thiotaurine were administered to rats every day over a long period of 180 days, not only were there no deaths at all, but no change in the body weight curve was observed, either.

Also, in an acute toxicity experiment using SD male and female rats, oral $LD_{50}$ was found to be over 2,000 mg/kg. Further, in a reverse mutant experiment (Ames Test) using bacteria, no mutagenecity was observed in either coexistence or non-coexistence with S9Mix. In addition, the result was determined to be negative in both a primary skin irritation test and an eye irritation test using rabbits.

Thus, a compound according to the present invention may be used as a safe and effective treatment or preventive agent against diseases in humans or animals which are thought to be caused by active oxygen. Therefore, a compound according to the present invention may be effectively used as, for example, an active oxygen scavenger, a dermatologic preparation.

An active ingredient compound according to the present invention may be administered as an application preparation, orally, or by any parenteral method. When given by application of in another manner, the medication method is not limited to any particular type regardless of the respective bases used, and any type preparation may be made according to conventional methods.

For example, the various types of oral administration which may be used include tablets, pills, granules, soft/hard capsules, dusting powders, fine granules, powders, emulsions, suspensions, syrups, pellets, elixirs, etc. The types of parenteral administration which may be used include injections, drips, transfusions, pastes, lotions, tonics, sprays, suspensions, oils, emulsions, suppositories, etc. Preparation of the effective ingredient according to the present invention may be done following a conventional procedure, using a surfactant, excipient, coloring agent, perfume, preservative, stabilizer, buffer, or suspending agent, isotonizing agent or another conventionally used auxiliary. The same applies to a external preparations.

The amount of the medicinal composition to be administered differs depending on its kind, the kind of disorder, the method of administration, the age and symptoms of the patient, and the length of the treatment period. The range of the amount per day per adult is 0.01–2000 mg/kg, and preferably 0.1–1000 mg/kg for intravenous injection; 0.01–3000 mg/kg, and preferably 0.1–1500 mg/kg for intramuscular injection; and 0.5–4000 mg/kg, and preferably 1–2000 mg/kg for oral administration. When used as a dermatologic preparation, it should be applied in a proper amount to the affected part following usual methods.

The following are examples of applications and other types of preparation according to the present invention.

Example 1: Preparation of Creams

Cream was prepared by adding purified water to the ingredients (1)–(10) listed in Table 11 below to make a total amount of 100 g.

TABLE 11

Composition of cream

|  |  | (g) |
|---|---|---|
| (1) | Vaseline | 2.5 |
| (2) | Liquid paraffin | 10.0 |
| (3) | Cetostearyl alcohol | 12.0 |
| (4) | Polyoxyethylene sorbitan monostearate | 7.0 |
| (5) | Sorbitan monostearate | 1.0 |
| (6) | Propylene glycol | 5.0 |
| (7) | Aminoethyl thiosulfonate (thiotaurine) | 1.0 |
| (8) | Aminoethyl sulfinate (hypotaurine) | 0.5 |

TABLE 11-continued

| | Composition of cream | |
|---|---|---|
| | | (g) |
| (9) | Potassium pantetheine-sulfonate | 0.5 |
| (10) | Preservative and perfume | Appropriate |

Example 2: Preparation of Tablets

Of the ingredients (1)–(4) shown in Table 12 below, first ingredients (1), (2) and (3) (17 g) were mixed together, and were granulated together with a paste made from ingredient (3) (7 g). Ingredients (3) (5 g) and (4) were then added to the obtained granules and mixed well, and the mixture was compressed using a compression tableting machine, to prepare 1000 tablets each containing 50 mg of the active ingredient (1).

TABLE 12

| | Composition of tablets | |
|---|---|---|
| | | (g) |
| (1) | Dimethylthiotaurine | 50 |
| (2) | Lactose | 90 |
| (3) | Corn starch | 29 |
| (4) | Magnesium stearate | 1 |

Example 3: Preparation of Injections

All of the ingredients (1)–(4) listed in Table 13 were dissolved in 1000 ml of distilled water, after which the solution was distributed into 1 ml ampules to produce 1000 injections.

TABLE 13

| | Composition of injections | |
|---|---|---|
| | | (g) |
| (1) | Sodium N-lauroylthiotaurine | 5 |
| (2) | Sodium chloride | 9 |
| (3) | Chlorobutanol | 5 |
| (4) | Sodium hydrogen carbonate | 1 |

EFFECTS OF THE INVENTION

According to the present invention, it is possible to prevent and/or treat a wide range of disorders caused by active oxygens and free radicals, and since it causes no medicinal or cosmetic damage, it is fully safe to use.

We claim:

1. A method for scavenging active oxygen compounds comprising applying to the skin of a living body an effective amount for inhibiting ultraviolet B rays for scavenging active oxygen compounds of a compound of the formula:

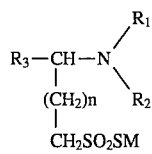

wherin $R_1$ and $R_2$ may be identical or different, each representing a hydrogen atom, a saturated or unsaturated linear or branched alkyl or acyl group of from 1–22 carbon atoms, or an amidino group;

$R_3$ represents a hydrogen atom or —$COOR_4$, where $R_4$ represents a hydrogen atom, a saturated or unsaturated linear or branched alkyl group with carbon number 1–22, or an alkali metal or alkaline earth metal; M represents a hydrogen atom or an alkali metal; and n represents either 0 or 1.

2. A method for inhibiting ultraviolet B rays comprising applying to the skin of a living body an effective amount for inhibiting ultraviolet B rays of a compound of the formula;

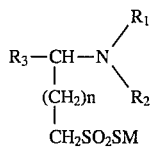

wherein $R_1$ and $R_2$ may be identical or different, each representing a hydrogen atom, a saturated or unsaturated linear or branched alkyl or acyl group of from 1–22 carbon atoms, or an amidino group;

$R_3$ represents a hydrogen atoms or —$COOR_4$, where $R_4$ represents a hydrogen atom, a saturated or unsaturated linear or branched alkyl group with carbon number 1–22, or an alkali metal or alkaline earth metal; M represents a hydrogen atom or an alkali metal; and n represents either 0 or 1.

3. A method for inhibiting erythema from ultraviolet B rays comprising applying to the skin of a living body an effective amount for inhibiting ultraviolet B rays of a compound to inhibit erythema from ultraviolet B rays of the formula

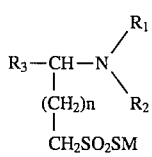

wherein $R_1$ and $R_2$ may be identical or different, each representing a hydrogen atom, a saturated or unsaturated linear or branched alkyl or acyl group of from 1–22 carbon atoms, or an amidino group;

$R_3$ represents a hydrogen atom or —$COOR_4$, where $R_4$ represents a hydrogen atom, a saturated or unsaturated linear or branched alkyl group with carbon number 1–22, or an alkali metal or alkaline earth metal; M represents a hydrogen atom or an alkali metal; and n represents either 0 or 1.

* * * * *